United States Patent
Walls et al.

(10) Patent No.: US 10,324,039 B2
(45) Date of Patent: Jun. 18, 2019

(54) FLUID CHARACTERIZATION OF POROUS MATERIALS LIBS

(71) Applicant: Ingrain, Inc., Houston, TX (US)

(72) Inventors: Joel Walls, Houston, TX (US); Kathryn Elizabeth Washburn, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 440 days.

(21) Appl. No.: 14/948,442

(22) Filed: Nov. 23, 2015

(65) Prior Publication Data
US 2016/0146738 A1   May 26, 2016

Related U.S. Application Data

(60) Provisional application No. 62/083,940, filed on Nov. 25, 2014.

(51) Int. Cl.
| | | |
|---|---|---|
| *G01N 21/71* | (2006.01) | |
| *G01N 33/24* | (2006.01) | |
| *G01N 33/28* | (2006.01) | |

(52) U.S. Cl.
CPC ......... *G01N 21/718* (2013.01); *G01N 33/241* (2013.01); *G01N 33/246* (2013.01); *G01N 33/2823* (2013.01); *G01N 2201/129* (2013.01)

(58) Field of Classification Search
CPC .......... G01N 21/718; G01N 2201/129; G01N 33/241; G01N 33/246; G01N 33/2823
USPC ........................................... 356/70
See application file for complete search history.

(56) References Cited

U.S. PATENT DOCUMENTS

| | | | |
|---|---|---|---|
| 8,081,796 B2 | 12/2011 | Derzhi et al. | |
| 8,170,799 B2 | 5/2012 | Dvorkin et al. | |
| 8,302,683 B2 * | 11/2012 | Pfeiffer | E21B 43/40 166/246 |
| 9,506,869 B2 * | 11/2016 | Quant | G01N 21/718 |
| 2003/0106995 A1 | 6/2003 | Smith et al. | |
| 2008/0151241 A1 | 6/2008 | Lindfors et al. | |

(Continued)

FOREIGN PATENT DOCUMENTS

| | | |
|---|---|---|
| CN | 101984344 A1 | 3/2011 |
| CN | 103293024 A1 | 9/2013 |

(Continued)

OTHER PUBLICATIONS

International Search Report and Written Opinion issued in corresponding International Patent Application No. PCT/US2015/062069 dated Mar. 21, 2016 (15 pages).

(Continued)

*Primary Examiner* — Hina F Ayub
*Assistant Examiner* — Amanda Merlino
(74) *Attorney, Agent, or Firm* — Chamberlain Hrdlicka

(57) ABSTRACT

A method for analyzing fluid characteristics of a geological sample with laser-induced breakdown spectral measurements performed on the geological sample, spectral preprocessing performed as necessary, and subsequent analysis is applied to the collected data to determine at least one fluid parameter of the sample. The method can provide a more rapid and reliable method to estimate fluid properties of a geological sample. A system for performing the method also is provided.

14 Claims, 8 Drawing Sheets

(56) References Cited

U.S. PATENT DOCUMENTS

| | | | |
|---|---|---|---|
| 2013/0070242 A1* | 3/2013 | Liu | G01N 21/718 356/318 |
| 2013/0199847 A1* | 8/2013 | Delmar | E21B 25/00 175/44 |
| 2015/0323516 A1 | 11/2015 | Washburn | |
| 2015/0323517 A1 | 11/2015 | Washburn | |
| 2016/0054284 A1* | 2/2016 | Washburn | G01J 3/443 356/318 |

FOREIGN PATENT DOCUMENTS

| | | |
|---|---|---|
| WO | 2004/003595 A1 | 1/2004 |
| WO | 2013/023299 A1 | 2/2013 |
| WO | 2013/071188 A1 | 5/2013 |

OTHER PUBLICATIONS

Bousquet et al., "Development of a mobile system based on laser-induced breakdown spectroscopy and dedicated to in situ analysis of polluted soils," Spectrochimica Acta Part B, vol. 63, 2008, pp. 1085-1090.

Seo et al., "Microanalysis of S, Cl, and Br in fluid inclusions by LA-ICP-MS," Chemical Geology, vol. 284, 2011, pp. 35-44.

Koujelev et al., "Artificial Neural Networks for Material Identification, Mineralogy and Analytical Geochemistry Based on Laser-Induced Breakdown Spectroscopy," Artificial Neural Networks—Industrial and Control Engineering Applications, Intech, Apr. 4, 2011, pp. 91-116.

Lalanne et al., "How to Cope with some of the Challenges Associated with Laboratory Measurements on Gas Shale Core Samples," SPE 167709, SPE/EAGE European Unconventional Conference and Exhibition, Vienna, Austria, Feb. 25-27, 2014 (17 pages).

Nordeng, "Evaluating Source Rock Maturity Using Multi-Sample Kinetic Parameters from the Bakken Formation (Miss.-Dev.), Williston Basin, ND," Geol. Investig. No. 164, North Dak. Geol. Survey, 2013, pp. 1-19 (19 pages).

Peters, "Guidelines for Evaluating Petroleum Source Rock Using Programmed Pyrolysis," The American Association of Petroleum Geologist Bulletin, V. 70, No. 3, Mar. 1986, pp. 318-329 (12 pages).

Bellucci et al., "A detailed geochemical investigation of post-nuclear detonation trinitite glass at high spatial resolution: Delineating anthropogenic vs. natural components," Chemical Geology 365, 2014, pp. 69-86 (18 pages).

Tiwari et al., "Detailed Kinetic Analysis of Oil Shale Pyrolysis TGA Data," AIChE Journal, Feb. 2012, vol. 58, No. 2, DOI 10.1002/aic, pp. 505-515 (11 pages).

Lalanne et al., "Benefits of High-Resolution Core Logs Integration in Characterizing Gas Shales Cores", International Symposium of the Society of Core Analysts, SCA Paper No. 2013-076, Sep. 2013 (6 pages).

Grader et al., "Computations of Porosity and Permeability of Sparic Carbonate Using Multi-Scale CT Images," International Symposium of the Society of Core Analysts, SCA2009—Temp Paper #03-10, Sep. 27-30, 2009, pp. 1-10.

Handwerger et al., "Methods Improve Shale Core Analysis," The American Oil & Gas Reporter, Dec. 2012: pp. 1-12.

\* cited by examiner

FLUID CHARACTERIZATION OF POROUS MATERIALS LIBS

This application claims the benefit under 35 U.S.C. § 119(e) of prior U.S. Provisional Patent Application No. 62/083,940, filed Nov. 25, 2014, which is incorporated in its entirety by reference herein.

FIELD OF THE INVENTION

The present invention relates to a method to quantify and characterise fluids saturating porous geological materials using laser-induced breakdown spectroscopy. The present invention also relates to a system for the method.

BACKGROUND OF THE INVENTION

Fluid saturation of porous materials is important to evaluate and model a reservoir in general. Saturation is the ratio of the pore volume occupied by a fluid phase to the total pore volume. Knowing initial fluid saturations will help validate simulations and confirm that assumed wettability values are reasonable. In general for the industry, current fluid characterization methods tend to be slow and error prone, particularly for very low permeability materials like shale.

In addition, characterization of the fluids, such as composition, viscosity, pour point, etc. for the oil and salinity for the brine are important factors for calibration (e.g. for resistivity) and understanding the economics and production of a reservoir.

Fluid saturation is important for understanding the economics, history, and optimization of production from a reservoir. In addition to their quantities, understanding the properties of the fluids therein helps determine the economics, guide the production methods, and determine the ultimate recovery. Brine salinity is important for calibration of petrophysical models involving resistivity data as well as preventing the use of fluids during drilling, completion, and production (e.g. drilling mud) that may cause damage to the reservoir (e.g. swelling of clays).

The standard way of determining fluid saturations is the Dean-Stark extraction technique. There are a variety of setups, but it generally involves cleaning samples in a solvent and measuring produced water. In one set-up, for example, the sample is placed in an extraction apparatus and the solvent is heated. Vapor of the solvent rises through the core and leaches out the oil and water. Water condenses and is collected, such as in a graduated cylinder. A typical solvent is toluene, miscible with the oil but not the water. Solvent and oil continuously cycle through the extraction process. The volume of water collected is recorded and when the reading becomes constant, the heating is discontinued. The water saturation ($S_w$) in the core is determined from direct measurements performed on the sample, such as the ratio of the measured collected water and the difference of the dry sample weight and fresh water resaturated weight, whereas the hydrocarbon saturation ($S_o$) is inferred by a calculation using the water saturation, the sample porosity, and other determined parameters for the sample. This method is time consuming, error prone (leaking, etc.) and requires a significant amount of sample. It has a higher error margin in low porosity and low permeability samples.

Determining fluid saturation via Dean-Stark limits further use of the cores for other kinds of analysis since all the native fluids have been removed from the sample before it is resaturated with fresh water.

Other methods include centrifuging out fluids. However, there is usually residual fluid left in the core that cannot be produced, such that this gives only a qualitative estimation of the fluid saturations.

Nuclear Magnetic Resonance (NMR) has been used as a non-destructive method for fluid saturations. Common methods use a two dimensional measurement that correlates the measured diffusion coefficient with the transverse relaxation time. Because gas has a higher diffusion coefficient than water, and in turn oil, the diffusion coefficient can be used to help separate system constituents. However, this method is frequently inconclusive in its evaluation of system fluids, as there are many competing effects that influence the NMR response.

Retort methods are also frequently used to determine sample saturation. This is performed by heating the sample in stages up to some high temperature. The exact times and temperatures will vary between labs. However, it is assumed that the fluids at a certain temperature arise from only a certain class of water (e.g. claybound). Retort measurements are frequently run in the span of an hour, which may not completely desiccate the samples and leads to uncertainty in the response. This technique also does not allow the further use of a sample in a given saturation state.

For conventional reservoir samples, it is frequently straightforward to obtain a water sample and determine its salinity. However, in shale reservoirs, obtaining a brine sample is often difficult. The samples do not easily produce water and the amounts tend to be small. Large quantities of sample are frequently required to estimate reservoir salinity and the extractions, via centrifugation or Dean-Stark, take extended periods of time.

Dielectric measurements are also used to estimate the sample salinity, but this requires detailed information on the sample composition and sometimes structure in order to estimate accurately. Textural effects in the sample may also lead to uncertainty in the dielectric response.

Laser induced breakdown spectroscopy (LIBS) uses a laser to ablate a tiny portion of sample. LIBS has been used to provide identification of materials and chemical compositions of solid materials. The standard for LIBS uses a q-switched solid state laser that produces a rapid pulse, typically on the order of pico- to nanoseconds in duration. Optics are used to focus the energy onto a single spot on the sample. A strong laser ablates a small portion of the sample, turning it into a high temperature plasma. The excited atoms then return to a ground state, giving off light of characteristic frequencies. The spot size vaporized by the laser can range in size from a few microns up to hundreds of microns, allowing a large range and is dependent on the optics of the system. The signal improves with larger spot size, but sacrifices resolution. While a small amount of sample is consumed, the amount is so small that it is considered to be negligible and the technique is considered non-destructive.

The wavelength of light from the plasma is typically measured in the 200 nm to 980 nm region. The resulting spectra can be analysed by multivariate data to correlate the spectra to concentration of elements. LIBS has been used previously as a method for mineralogy identification, making it an alternative to XRD and XRF methods for mineralogical analysis of samples. It has an advantage over XRF for mineralogical identification because it can measure all elements, whereas XRF is unable to detect light elements.

LIBS is able to perform depth profiling, firing the laser in the same spot, and observing the different products that are produced with increased depth. LIBS is also very rapid, taking only seconds per measurement and making it amenable for high-throughput industrial use. LIBS measurements can be rastered to produce a two dimensional map of surface composition.

SUMMARY OF THE INVENTION

A feature of the present invention is to use LIBS to quantify the amount and types of fluids saturating porous materials. As a further feature, the invention can be used to estimate properties of the saturating fluids, such as, but not limited to, salinity and salt typing for water and density, API, viscosity, pour point and trace element content (e.g. sulphur) for oils.

To achieve these and other advantages and in accordance with the purposes of the present invention, as embodied and broadly described herein, the present invention relates, in part, to a method for analysing a geological sample, comprising subjecting at least the fluid contents of at least one location of the geological sample to a plurality of successive measurement shots of laser light with each measurement shot at least partly vaporising and ionising the sample to cause spectral emission; detecting the spectral emission after each measurement shot with at least one spectrum detector to collect raw spectral data; optionally pre-processing the collected raw spectral data from the spectrum detector in order to transform the raw spectral data into a more suitable form for subsequent analysis; optionally analysing the raw or preprocessed spectral data; and determining at least one fluid parameter from the raw or preprocessed spectral data.

A system for performing the method is also provided.

It is to be understood that both the foregoing general description and the following detailed description are exemplary and explanatory only and are intended to provide a further explanation of the present invention, as claimed.

The accompanying figures, which are incorporated in and constitute a part of this application, illustrate various features of the present invention and, together with the description, serve to explain the principles of the present invention. The features depicted in the figures are not necessarily drawn to scale. Similarly numbered elements in different figures represent similar components unless indicated otherwise.

BRIEF DESCRIPTION OF THE DRAWINGS

FIGS. 1A-1C show the relationship between the hydrogen peak and the sodium peak for LIBS measurements on filter paper soaked in different concentrations of NaCl solutions, wherein FIG. 1A shows the hydrogen and sodium peaks for water (0% NaCl added), FIG. 1B shows the hydrogen and sodium peaks for a brine (5% NaCl), and FIG. 1C shows the hydrogen and sodium peaks for a brine of higher salt content (10% NaCl), where % are by weight % of brine.

DETAILED DESCRIPTION OF THE INVENTION

Figure 1A:
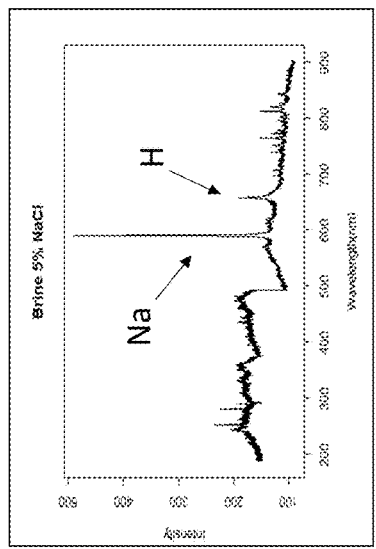

The present invention relates in part to a method to quantify and characterise fluids saturating porous geological materials using laser-induced breakdown spectroscopy (LIBS).

In addition to ablating material, some of the energy from the laser used in LIBS is transferred to the surrounding rock matrix. This serves to heat up fluids such as water, oil, and drilling mud in the surrounding pore space, such that they will volatise. The volatised materials can form a plasma that emits detectible light which is specific to the elemental composition, and the intensity of the emitted light can be correlated to the concentration of the element. In some cases, the laser shot preferentially volatiles the liquids over the solid matrix. Therefore, when the next shot is performed, there will be less fluid in the pore space, which will be observed by a change in the LIBS spectra. This is usually manifested by a loss of brine and hydrocarbon associated elements, such as hydrogen, carbon, oxygen, though there may be a loss of other elements as well. Again, the laser shot serves to heat up the system even more, driving off more fluid. Eventually, a steady state is likely to be reached, such that the LIBS spectra remains relatively constant with increasing shot number. This may be in regards to single elements such as hydrogen, carbon, oxygen, sodium, etc., or portions of the spectra or the whole spectra in its entirety. By comparing the initial spectra that includes elemental contributions from fluids to the final spectra where the liquids have been volatised, the liquid and solid responses can be separated. Fluid saturations can be estimated either through comparison to calibration sets created using previously characterized, known samples or by using mass balance to relate the change in H, C, and O from the starting LIBS measurements to the end LIBS measurements to water and hydrocarbon content. The volume of the different fluids present can be related to the change in intensity of the brine and hydrocarbon associated elements through comparison to a calibration set created from previously characterized, known samples. If the pore space is completely filled with brine and/or hydrocarbon, the ratio between the absolute volumes can be used to estimate water saturation ($S_w$) and hydrocarbon saturation ($S_o$). If the pore space is not completely filled with fluid (e.g., previously gas filled porosity now only contains air), relative fluid saturations can be determined by comparing the absolute volumes of brine and hydrocarbon calculated from LIBS to the total volume of pore space measured by another method. Further, classification of samples according to the kinds (phases) of saturating fluids can be determined using the LIBS measurements according to a method of the present invention.

The total volume of pore space can be determine through a variety of different methods including e.g., digital rock physics (digital imaging-based) methods, laboratory methods, or other methods, such as, but not limited to: x-ray computed tomography (CT), nuclear magnetic resonance (NMR), helium porosimetery, scanning electron microscopy (SEM), and focused ion beam (FIB)-SEM imaging, $N_2$ adsorption, from dried and resaturation weights, etc. For laboratory methods, as an option, total pore volume of a sample can be determined by a technique that has been used in conjunction with Dean-Stark methods, which involves drying the sample and weighing the resulting dried sample (e.g., $M_{dry}$ in grams), and then resaturating the dried sample with fresh water ($\rho=1.00$ g/cc) and weighing the resaturated sample ($M_{resat}$ in grams), and then pore volume (e.g., $V_p$ in cc) can be calculated as $(M_{resat}-M_{dry})/\rho$. Digital rock physics methods can be used to estimate total pore volume of a sample, such as by methods which provide 3D submicron pore network reconstruction, such as described in U.S. Pat. Nos. 8,170,799 B2 and 8,081,796 B2, and Grader, A. S., et al., "COMPUTATIONS OF POROSITY AND PERMEABILITY OF SPARIC CARBONATE USING MULTI-SCALE CT IMAGES, SCA2009-Temp Paper #03-10, Sep. 27, 2009, pages 1-10, which are all incorporated in their entireties by reference herein. As known, porosity can be defined as equal to ratio of pore volume/bulk volume (PHIt=Vp/Vb), so knowledge of one of porosity or pore volume can be readily converted to the other with further knowledge of the bulk volume of the sample. The bulk volume of the sample can be determined by laboratory methods (e.g., fluid displacement using Archimedes Principle) or digital rock physics. For the laboratory or digital rock physics determinations of pore volume, porosity, and/or bulk volume, it will be appreciated that a sample similar to the sample used for the LIBS measurements can be used for these analyses, or the same sample as used in the LIBS measurements since the LIBS measurements may only minimally ablate portions of the surface of the sample. Laboratory analyses methods, if used, preferably should follow the LIBS measurements if the same sample is being used.

The rate at which different fluids volatise will depend on their composition. Lighter fluids, such as water and natural gas condensate, volatise more easily than heavier fluids, such as viscous oils. Therefore, the change in the spectra can be used to estimate not only the volumes of the saturating fluids, but their properties as well. This may be estimated by the rate of change of elements such as hydrogen, carbon, and oxygen with shot number as the fluids are volatizing. As an option, by estimating a volume of pore water for a sample from the LIBS spectra, such as by comparing the LIBS H and O peaks or other peaks of an unknown sample with a calibration model based on the same or similar samples, but with known fluid compositions, then water saturation ($S_w$) can be determined, such as calculated as the ratio of the estimated pore water volume from the LIBS measurements/total pore volume. As an option, hydrocarbon or oil saturation ($S_o$) of the sample can be calculated from data developed from determining water saturation and other data, such as the ratio of: (the sample mass—the sample dry weight—the estimated sample water amount by LIBS)/(the total pore volume×oil density). Fluid properties may also be estimated using the ratios between hydrogen and carbon. This may be relatable to gas-chromatograph (GC) data.

One challenge with elemental measurements is distinguishing the effects of the fluid from that of the matrix. This may be compensated for in several ways. Models may be able to directly correct for the mineralogy of the sample. By observing any changes in mineralogy with shot number, LIBS can be used to help determine if any mineralogical aspects may be contributing to spectral changes and correct for them. This may be performed by comparing the LIBS signal for a fluid saturated sample to the LIBS signal from a dry sample or by using multivariate calibration models that have been created with LIBS measurements on different types of mineralogy, organic content, and fluid types and saturations. Results may be interpreted individually for a single LIBS measurement. Results may also include comparing the signal intensity between one or more shots of the laser. Shots of the laser from the sample point may be averaged to improve signal quality. In addition, the results may be compared to one or more samples in another saturation state (e.g., dry, cleaned, 100% water saturated, etc.) to help clarify the system response.

The technique may also help distinguish between hydrocarbon and bitumen. Cleaning of organic-rich shale samples to determine fluid saturations by laboratory methods may overestimate the oil saturation, because the cleaning process will also remove bitumen, which is immobile in-situ. With the method of the present invention, the signal from the liquid and the solid hydrocarbons should decay at different rates, allowing a better determination of what is producible and what is not.

LIBS measures elements. Sodium has a very prominent peak in the LIBS spectra. Measurements on samples show an increasing ratio of Na to H with increased brine salinity. By calibrating the Na to H (and optionally O) peaks, the brine salinity of the sample may be inferred or understood by comparing the sodium and hydrogen peaks in the detected spectrum emissions with the calibration. This may be possible with a single measurement, or multiple shots of the laser may be required. Comparison between samples in different saturation states may also be required. The presence and salt concentration of other metals, such as one or more, two or more, or three or more (e.g., Ca, Mg, K, Si, Fe, Al, and/or others such as any alkaline earth metal, transition metal, metals in the boron group, rare earths, heavy metals) may be determined similarly.

Sample desiccation can be an issue during measurement. Special sample pre-treatment, holders, or sample wrapping may need to be used in order to prevent problems of sample drying out before and during measurement.

Figure 1B:
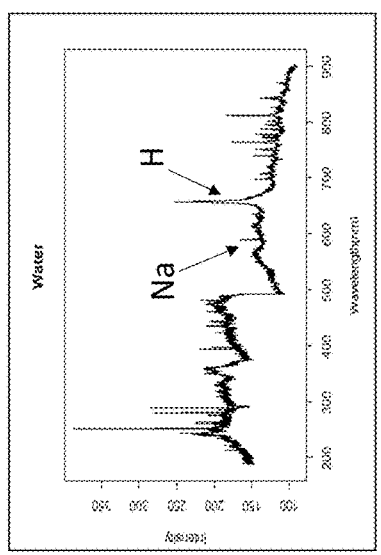
Figure 1C:
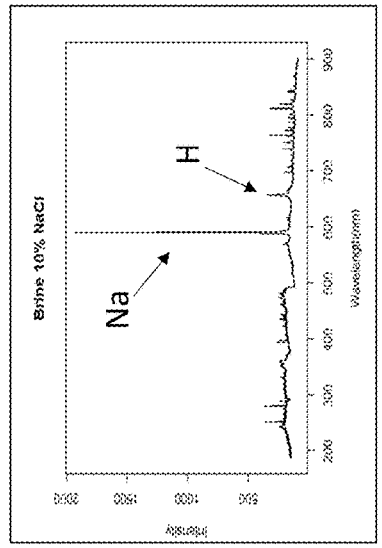
Figure 2:
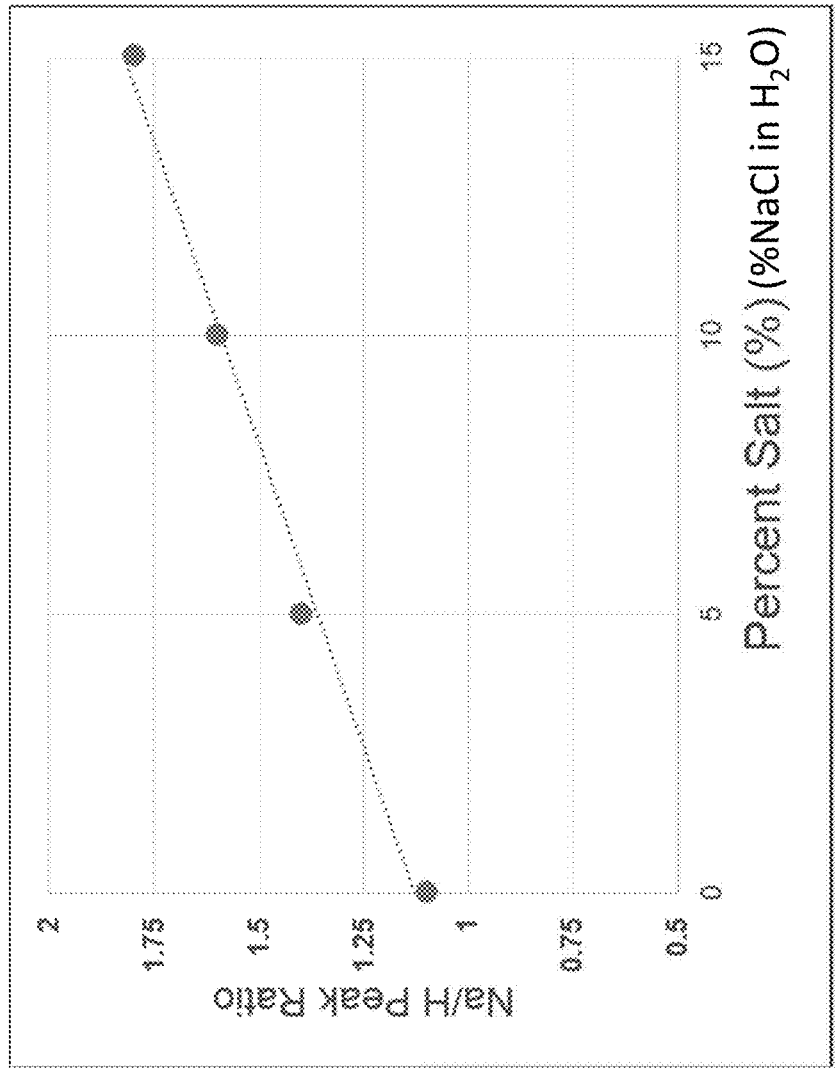
FIG. 2 shows the linear relationship between the LIBS hydrogen and sodium peaks as a function of NaCl concentration, with % being wt %.
Figure 3A:
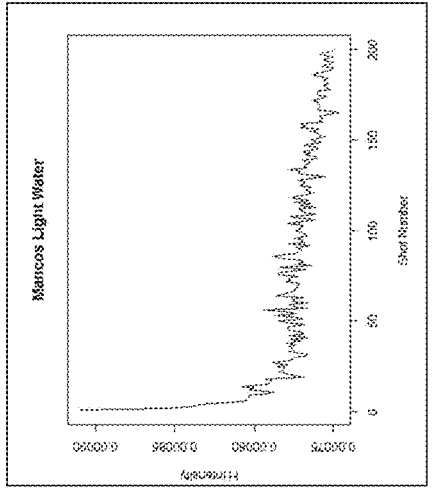
FIGS. 3A-3C show the different intensities and rates of change of the LIBS hydrogen peak for dry shale (FIG. 3A), shale saturated with water (FIG. 3B), and shale saturated with oil (FIG. 3C).
Figure 3B:
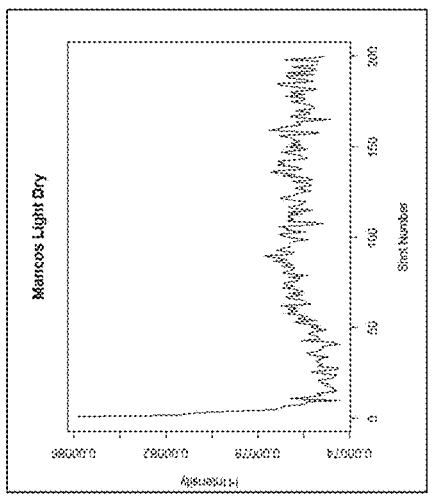
Figure 3C:
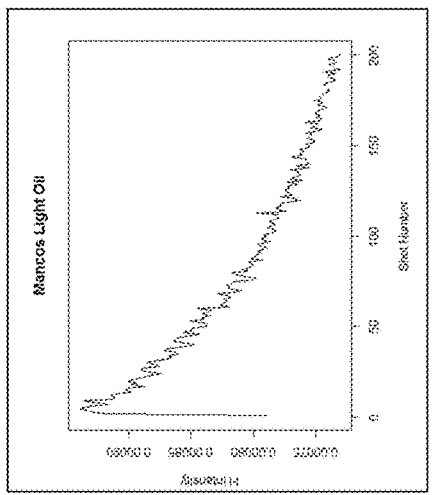
Figure 4A:
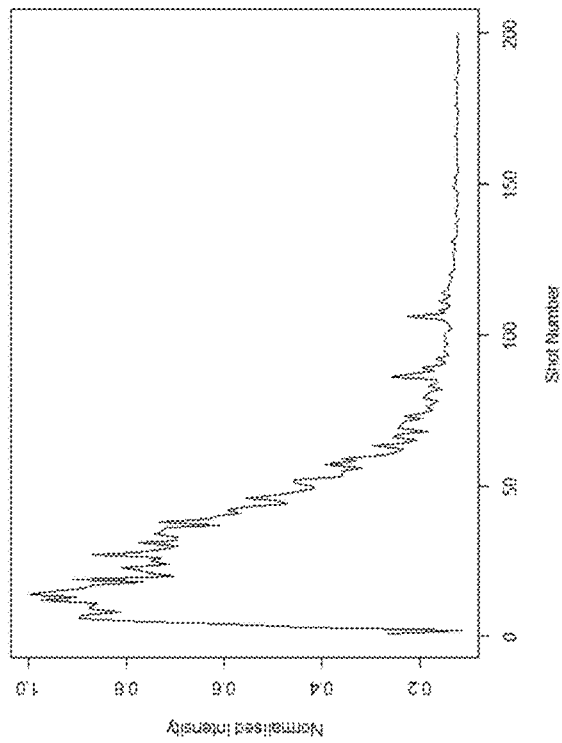
FIGS. 4A-4B shows the difference in rate of hydrogen loss measured via the LIBS spectra between a sandstone saturated with a light oil (FIG. 4A), and a sandstone saturated with a heavy oil (FIG. 4B).
Figure 4B:
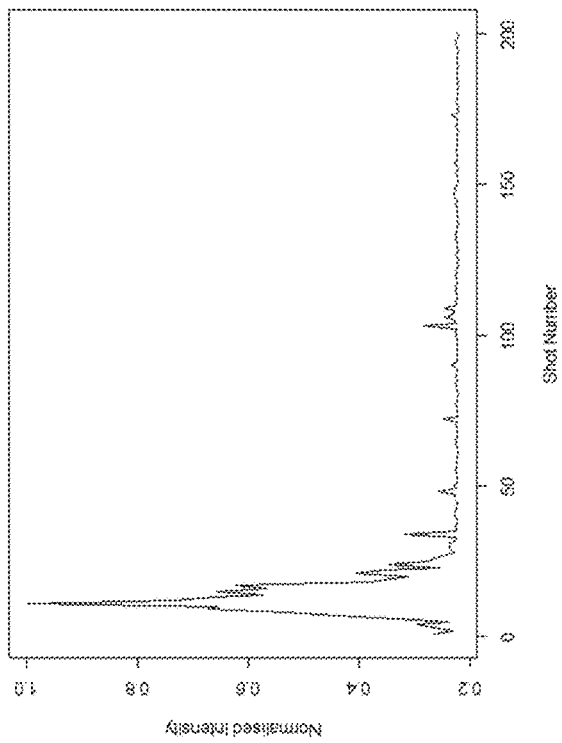

In addition to measurements performed to characterise fluids within the rocks, LIBS measurements can be used to characterise fluids that have been extracted from the rocks or other porous medium. As an option, fluids (e.g., water) can be extracted from samples, e.g. using solvent extraction techniques, such as used in the indicated Dean-Stark method, or using a centrifuge to force out fluids, etc. Measurements can be made directly upon the extracted fluids or upon material that has been saturated with the extracted fluids, e.g. filter paper. Preferably, the material used as a carrier for the extracted fluid does not interfere with or unduly complicate the plasma generation and spectral detection on the fluids in LIBS measurements. This measurement can be made when the material (carrier) is still wet or after it has been allowed to dry. This can be potentially used to give information on composition, salinity, different salt contents, viscosity, pour point, PVT properties, qualitative and quantitative sulfur content, qualitative and quantitative nitrogen content, qualitative and quantitative trace element content, qualitative and quantitative heavy metal content, etc. Using standards, which can be a range of different salinity solutions of known concentration, customized calibration and/or classification models can be created. These calibration and/or classification models can be used to correlate element concentrations for sodium, hydrogen, oxygen, and/or other elements with spectral peaks generated by LIBS measurements made on a sample of unknown fluid characteristics. As indicated, FIGS. 1A-1C show the relationship between the hydrogen peak and the sodium peak for LIBS measurements made on filter paper soaked in different concentrations of NaCl solutions (0% NaCl added, 5% NaCl, and 10% NaCl). FIG. 2 shows a calibration curve created from standards which can be brines of known composition (NaCl dissolved in water) and different NaCl concentrations wherein the ratio of the peaks for sodium to hydrogen is calibrated to a percent salt concentration.

Figure 5:
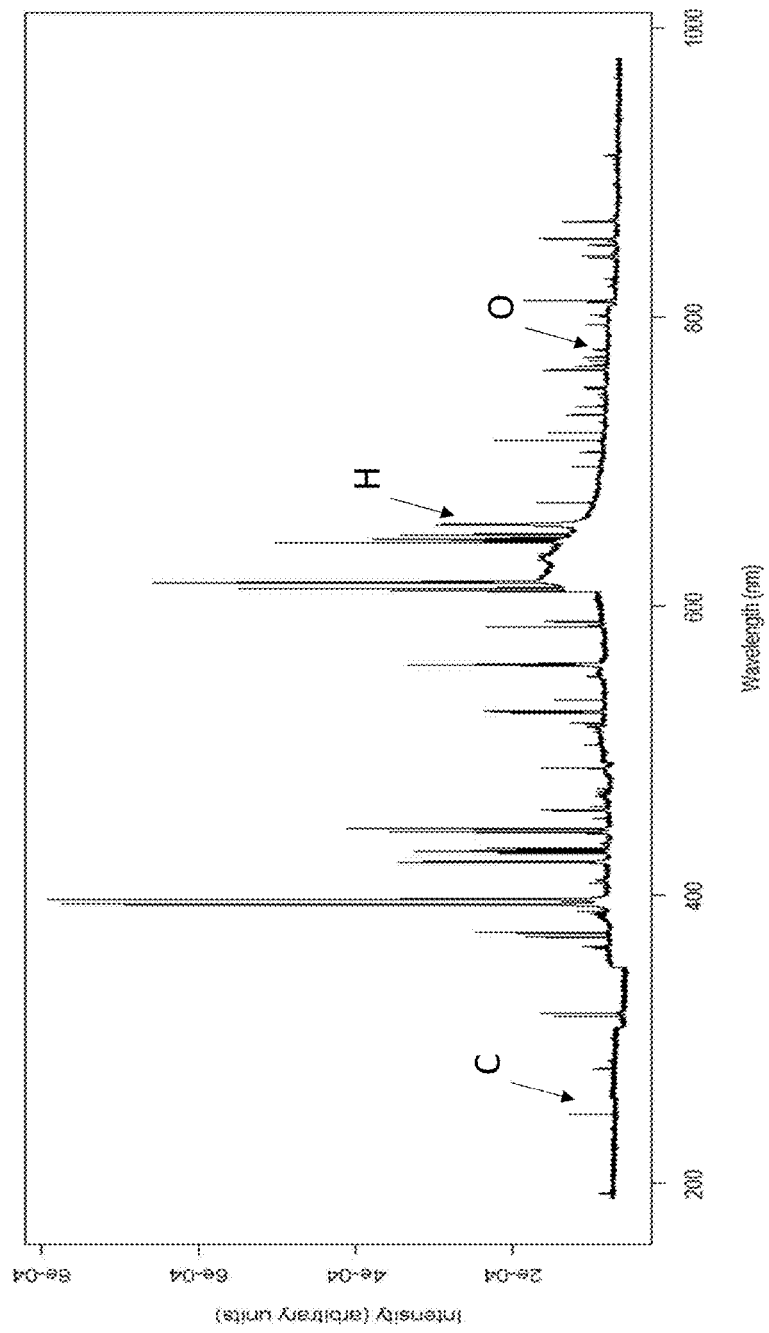
FIG. 5. shows an example LIBS spectrum for an oil saturated sample at the start of LIBS measurement, wherein the carbon (C), hydrogen (H), and oxygen (O) peaks are identified.
Figure 6:
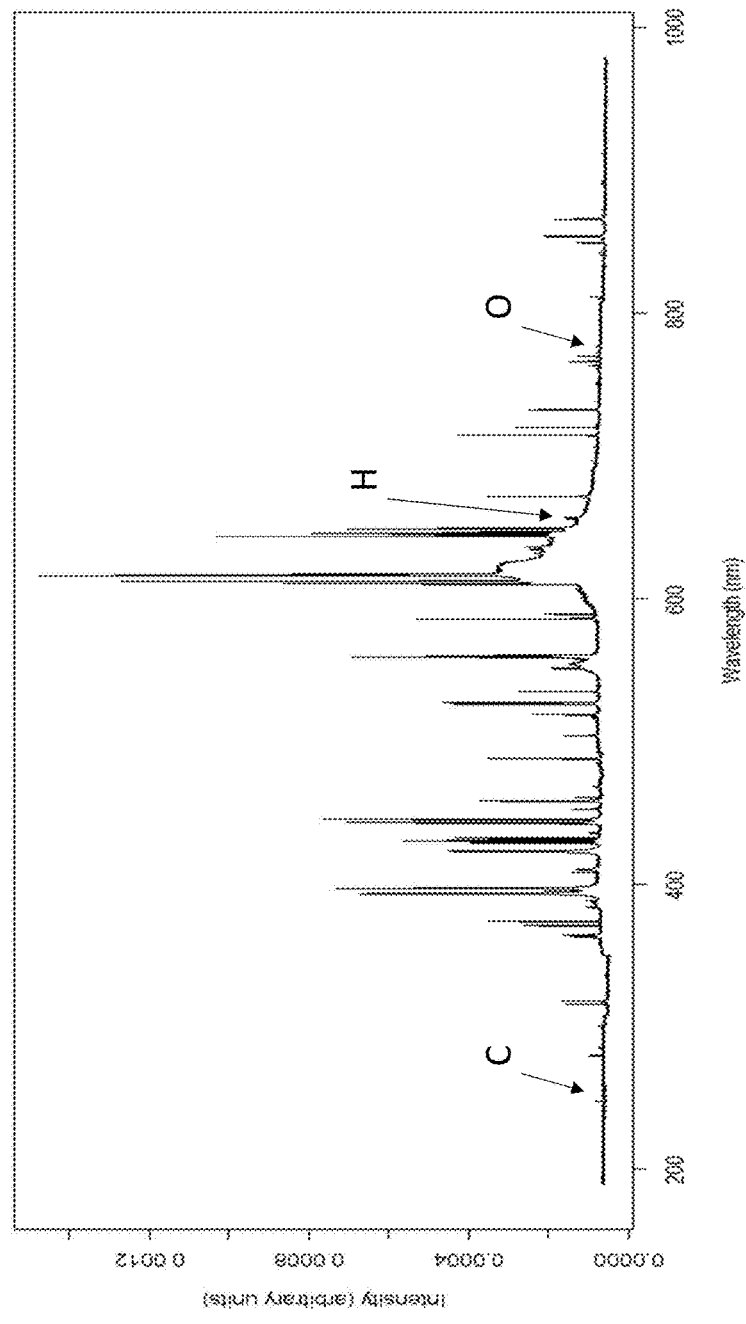
FIG. 6. shows an example LIBS spectrum for an oil saturated sample at the end of LIBS measurement. The loss of hydrogen, carbon, and oxygen between FIG. 5 can be observed.

FIGS. 3A-3C and 4A-4B show the effects on the respective intensities and rates of change profiles of the LIBS hydrogen peak for shale and sandstone samples that differ with respect to the presence of fluid or the kind of fluid if present. FIGS. 5 and 6 show examples of LIBS spectra for an oil saturated sample at the start of a LIBS measurement (e.g., within first five laser shots) and for an oil saturated sample at the end of the LIBS measurement (e.g., in final five laser shots), wherein the loss of hydrogen, carbon, and oxygen can be observed. As indicated, these effects can be used to develop calibration sets based on samples of known fluid characteristics for use in the analysis of a sample of unknown fluid characteristics.

Figure 7:
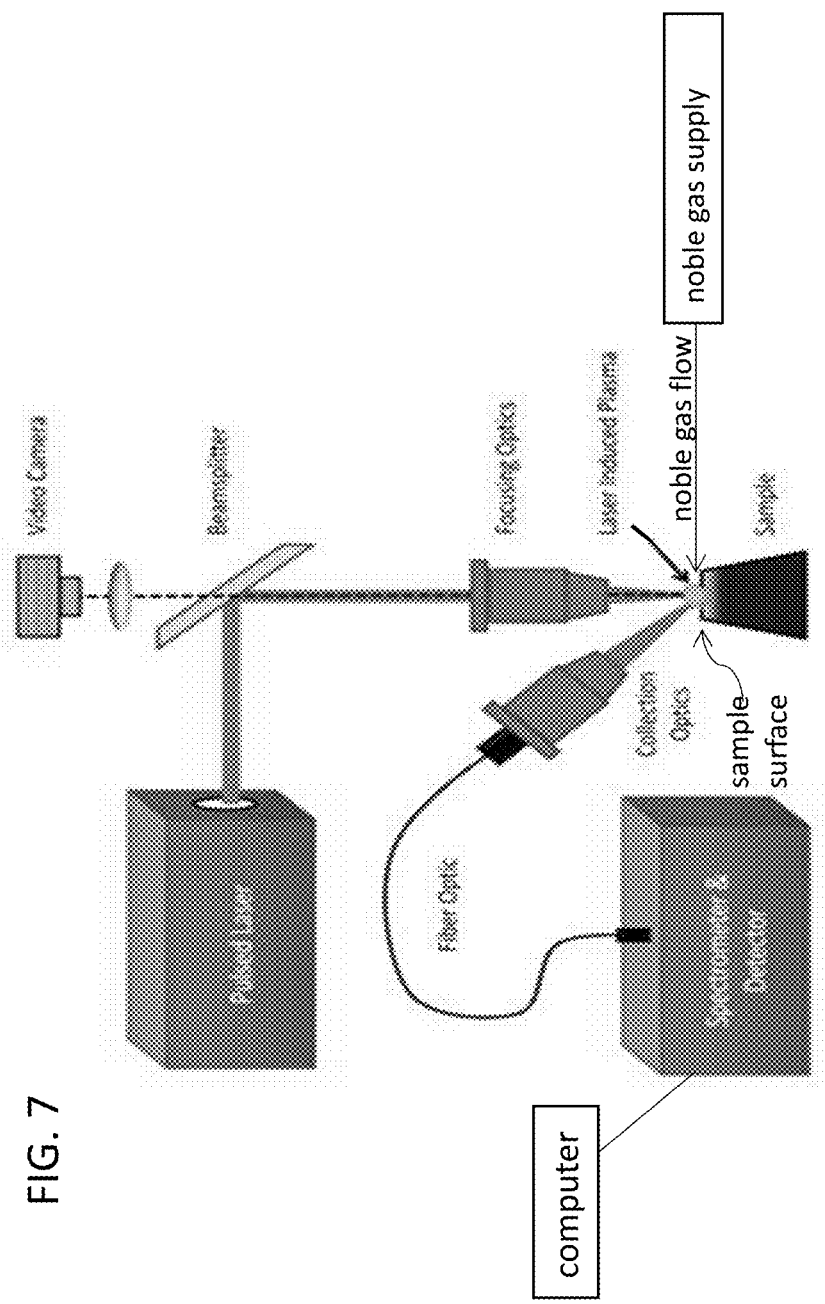
FIG. 7 shows an example setup of laser induced breakdown spectroscopy equipment according to an example of the present application.

As used in the examples of the present invention, a LIBS analyzer that has the configuration shown in FIG. 7 can be used. The LIBS analyser used can be commercially obtained from TSI Incorporated or other vendors of such devices. The measurements can be performed on TSI's latest model of LIBS analyzer, which has the name ChemReveal. Measurements can be made using a 200 mJ laser operating at 36 mJ power, or other powers. Shot rate can be one shot every 0.1 to 0.5 second, such as every 0.2 second, or other rates. Shot rate can be performed at 5 Hz and laser duration of 8 nanoseconds (ns), or other values. From about 10 to about 250 shots, or from about 20 to 100 shots of the laser, or other numbers of shots, including acquisition of the light spectra after each laser shot, can be measured. This appears to be adequate for most samples, though more or fewer shots may be required. Laser spot size on the sample can be 400 micrometers ($\mu m$), or other values. Samples can be placed on a three axis adjustable stage. A high-resolution camera can be used to adjust the sample stage to the correct distance for measurement and see where on the sample the laser would be fired. Argon may be supplied to continuously flow over the sample before measurement at a flow rate of from about 10 to about 12 liter/minute for a time period of from about 20 seconds to about 30 seconds prior to directing any laser shots onto the surface of the sample. Argon flow over the sample may be continued during LIBS measurement to avoid unwanted interference of elements commonly present in air (H, N, O, etc.) in the measurement. Analysis of the data may use all the acquired spectra or may be limited to a subset of the acquired spectra. Peaks which may be used for the analysis are one or more of an H peak located at about 656 nm, a C peak at about 247 nm, an O peak at about 777 nm, and/or a Na peak at about 590 nm.

The sample can be analysed as-is by the LIBS analyser or optionally one or a few cleaning shots may be applied to the location of the sample where the laser is targeted. Low level cleaning shots may be performed in order to remove surface imperfections or contaminants, but a weak power setting typically is used for any cleaning shots in order to avoid pyrolysation of any nearby organic matter. After any cleaning shots, multiple shots of the laser can be performed in rapid succession for vaporization of the fluid in the pores and detection of the spectral emissions.

The collected data from the spectral measurements can be pre-processed in order to make the raw LIBS data suitable for subsequent analysis to produce one or more fluid properties. Pre-processing, for example, can be performed by integration of peak area associated with a given element to produce an intensity curve for the element as a function of laser shot number. This can be performed for one or more peaks, either associated with the same element or different elements. The preprocessing can also comprise, for example, analysing the peak maxima associated with an element to produce an intensity curve with laser shot number for one or more elements, sub-selecting actual peak spectra for successive measurement shots, or sub-regions of the spectra or the whole spectra for the successive measurement shots, or compiling the data from the successive laser shots into a matrix, single vector, or other combined form. Pre-processing may also include applying an exponential fitting, bi-exponential fitting, multiple-exponential fitting, an inverse Laplace transform, a Gaussian decay fitting, or other analysis or filter or function to the data, such as taking a derivative, or removing data that do not meet quality control standards. Pre-processing may include a combination of any two or more of these listed steps. Uni-, cluster, multi-variate analysis, neutral nets, self-organising maps, metaheuristic procedures (e.g. particle swarm optimization, genetic algorithms, etc.) or manual analysis can be applied to raw or pre-processed data to produce fluid properties.

The geometry and size of the geological sample which is analysed with the LIBS analyser is not necessarily limited as long as it can be fitted on the sample positioning stage of the LIBS with adequate clearance with respect to the laser and collection optics. The sample can have a regular shape or an irregular shape. The sample can be a source of a rock formation sample, e.g., a drill cutting, sidewall core, microcore, outcrop quarrying, subsample of a whole core such as a core plug, or other subsamples, which can provide suitable samples for analysis using methods according to the present invention. The sample can have at least one flattened or nonflattened surface which can be used as the face of the sample which is impinged with the laser. The sample can have a regular shape, such as cubic, prismatic, cylindrical, disc, or others. As an option, the side dimension of the sample shape, if cubic, can be from 6.35 mm (0.25 inch) to 19 mm (0.75 inch), or other values outside of this range. The sample may have an irregular shape, and may have the shape of the originally obtained sample, such as a drill cutting.

The sample, that can be analysed using the method of the present invention, can be a porous medium that has interconnected pores, isolated pores, or both types of pores. The surface of a sample may be scouted using digital imaging (e.g., x-ray CT scanning, SEM) to identify a location or locations of particular interest for analysis by the method of the present invention.

Figure 8:
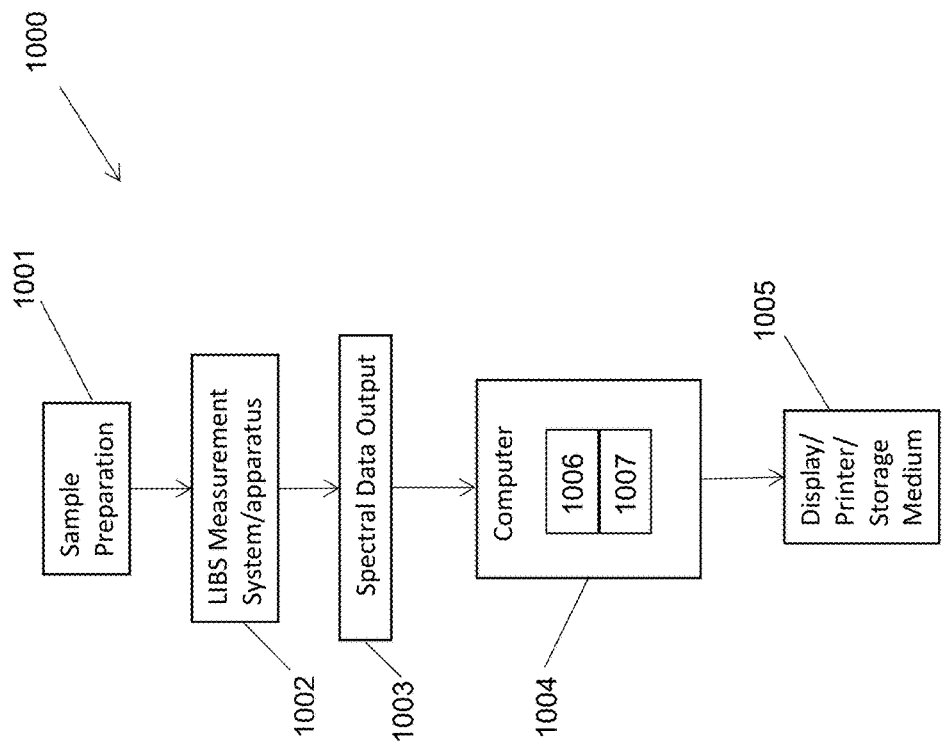
FIG. 8 shows a system according to an example of the present application.

The present invention also relates to a system for analyzing a sample of petroleum source or reservoir rock, such as according to the processes described herein. As illustrated in FIG. 8, for example, the system 1000 can include a sample preparation station 1001, at least one LIBS Measurement system/apparatus 1002 (e.g., such as shown in more detail in FIG. 7). The sample preparation 1001 can refer to obtaining a subsample of smaller size and/or desired shape from a larger geological sample. This step can be optional depending on the size, shape, and condition of the original sample. The one or more computer systems 1004 can be provided for processing of spectral data 1003 obtained from the LIBS measurement system 1002, according to methods of the present invention, and to output the results to at least one output device 1005 to display, print, or store results, or any combinations thereof, of the spectral data and results of computations based thereon using a method of the present invention. The computer 1004 can comprise at least one at least one non-transitory computer usable storage medium 1006 and at least one processor 1007. A computer program or programs used for spectral data analysis, preprocessing of data, and optionally other data analysis, and the computations can be stored, as a program product, on the least one non-transitory computer usable storage medium 1006 (e.g., a hard disk, a flash memory device, a compact disc, a magnetic tape/disk, or other media) associated with at least one processor (e.g., a CPU) which is adapted to run the programs, or may be stored on an external non-transitory computer usable storage medium which is accessible to the computer processor. The computer usable storage medium 1006 can include a stored program comprising a set of instructions which can be performed by the processor or processors for executing process steps of the present invention that involve spectral data analysis (e.g., LIBS data analysis) and computations based thereon. Input data and output data, and other program results, or combinations of these also can be stored on the at least one non-transitory computer usable storage medium or other non-transitory storage media. The computer 1004 may include one or more system computers, which may be implemented as a single personal computer or as a network of computers. However, those skilled in the art will appreciate that implementations of various techniques described herein may be practiced in a variety of computer system configurations, including hypertext transfer protocol (HTTP) servers, hand-held devices, multiprocessor systems, microprocessor-based or programmable consumer electronics, network PCs, mini-computers, mainframe computers, and the like. The indicated units/equipment of system 1000 can be connected to each other for communications (e.g., data transfer, etc.), via any of hardwire, radio frequency communications, telecommunications, internet connection, or other communication means. The indicated system or apparatus of the present invention may be suitable for analysing material in a laboratory or other space in a building, or in-the-field, such as in a mobile transport vehicle or mechanism on the ground or underground.

The present invention includes the following aspects/embodiments/features in any order and/or in any combination:

1. The present invention relates to a method for analysing a geological sample, comprising:
    a) subjecting at least the fluid contents of at least one location of the geological sample to a plurality of successive measurement shots of laser light with each measurement shot at least partly vaporising and turning the portion of said sample into plasma to cause spectral emission;
    b) detecting said spectral emission after each said measurement shot with at least one spectrum detector to collect raw spectral data;
    c) optionally preprocessing of the raw spectral data from the spectrum detector in order to transform the raw spectral data into a form for subsequent analysis; and
    d) determining at least one fluid parameter using the raw spectral data from the spectrum detector.
2. The method of any preceding or following embodiment/feature/aspect, wherein the at least one fluid parameter is water saturation, oil saturation, salinity, or any combinations thereof.
3. The method of any preceding or following embodiment/feature/aspect, wherein the at least one fluid parameter is salinity weight concentration, salinity salt typing, or both, for water.
4. The method of any preceding or following embodiment/feature/aspect, wherein the at least one fluid parameter is density, American Petroleum Institute (API) gravity, viscosity, pour point, trace element content (e.g., sulphur), or any combinations thereof, for oil.
5. The method of any preceding or following embodiment/feature/aspect, wherein the plurality of successive measurement shots of laser light are applied at a shot rate of one shot every 0.1 to 0.5 second for 10 to 250 shots of the laser.
6. The method of any preceding or following embodiment/feature/aspect, further comprising extracting the fluid contents from the at least one location before the subjecting, wherein the subjecting is performed on the extracted fluid contents.
7. The method of any preceding or following embodiment/feature/aspect, wherein the at least one fluid parameter is brine salinity determined by calibrating sodium (Na) to hydrogen (H) peaks and comparing the sodium and hydrogen peaks in the detected spectrum emissions with the calibration.
8. The method of any preceding or following embodiment/feature/aspect, wherein the pre-processing is performed and comprises integration of one or more peak areas to produce an intensity curve or curves, selection of the maxima of a peak for successive shots to produce an intensity curve, the actual peak spectra for successive measurement shots, or sub-regions of the spectra or the whole spectra for the successive measurement shots. Pre-processing may include two or more of the mentioned steps.
9. The method of any preceding or following embodiment/feature/aspect, wherein the preprocessing is performed and comprises filtering, application of a function (e.g. taking a derivative), pre-treatment by applying an exponential fitting, bi-exponential fitting, multiple-exponential fitting, an inverse Laplace transform, a Gaussian decay fitting, compiling the data from the successive laser shots into a matrix, single vector, or other combined form. Pre-processing may include two or more of the mentioned steps.
10. The method of any preceding or following embodiment/feature/aspect, wherein the fluid parameter is obtained wherein manual or uni or multivariate analysis or cluster analysis or self-organising maps or neural nets or meta-heuristic procedures (e.g. particle swarm optimization, genetic algorithms, etc.) is utilized to correlate the collected data, raw or pre-processed, to determine values for at least one fluid composition, salinity, different salt contents, viscosity, pour point, PVT properties, qualitative and quantitative sulfur content, qualitative and quantitative nitrogen content, qualitative and quantitative trace element content, qualitative and quantitative heavy metal content.
11. The method of any preceding or following embodiment/feature/aspect, wherein said subjecting comprises controlling operation of the laser and a plurality of said spectrum detectors to simultaneously detect spectral emissions from the geological sample across a plurality of different spectral regions, and said analysing comprises determining the presence and amount of a plurality of different elements in the geological sample.
12. The method of any preceding or following embodiment/feature/aspect, wherein the sample is a rock sample.

13. The method of any preceding or following embodiment/feature/aspect, wherein each of the spectrum detectors comprises a spectrometer having a CCD detector associated therewith.

14. The present invention further relates to a system for analysing a geological sample, comprising i) a LIBS spectral data acquisition device for obtaining LIBS spectral information on at least one geological sample; ii) one or more computer systems comprising at least one processor and a non-transitory computer-readable medium including a stored program comprising a set of instructions performed by the processor for carrying out steps to obtain fluid parameter information on the sample used in i) using the spectral data; and iii) at least one device to display, print, and/or store as a non-transitory storage medium, results of the computations.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for analysing a geological sample, comprising:
    a) subjecting at least the fluid contents of at least one location of the geological sample to a plurality of successive measurement shots of laser light, with each measurement shot at least partly vaporising and turning the portion of the fluid contents with said geological sample into plasma to cause spectral emission;
    b) detecting said spectral emission after each said measurement shot with at least one spectrum detector to collect raw spectral data;
    c) preprocessing of the raw spectral data from the spectrum detector in order to transform the raw spectral data into a form for subsequent analysis;
    d) observing changes in the raw spectral data based on the plurality of successive measurement shots until a steady state of raw spectral data is reached, wherein the steady state indicates that the fluid contents are vaporized;
    e) comparing an initial spectra that includes elemental contributions from the fluid contents to a final spectra taken after reaching the steady state; and
    f) determining at least one fluid parameter using the compared data.

2. The method of claim 1, wherein the at least one fluid parameter is water saturation, oil saturation, salinity, or any combinations thereof.

3. The method of claim 1, wherein the at least one fluid parameter is salinity weight concentration, salinity salt typing, or both, for water.

4. The method of claim 1, wherein the at least one fluid parameter is density, American Petroleum Institute (API) gravity, viscosity, pour point, trace element content, or any combinations thereof, for oil.

5. The method of claim 1, wherein the plurality of successive measurement shots of laser light are applied at a shot rate of one shot every 0.1 to 0.5 second for 10 to 250 shots of the laser.

6. The method of claim 1, further comprising extracting the fluid contents from the at least one location before the subjecting, wherein the subjecting is performed on the extracted fluid contents.

7. The method of claim 1, wherein the at least one fluid parameter is brine salinity determined by calibrating sodium (Na) to hydrogen (H) peaks and comparing the sodium and hydrogen peaks in the detected spectrum emissions with the calibration.

8. The method of claim 1, wherein the pre-processing is performed and comprises integration of one or more peak areas to produce an intensity curve or curves, selection of the maxima of a peak for successive shots to produce an intensity curve, an actual peak spectra for successive measurement shots, or sub-regions of the spectra or the whole spectra for the successive measurement shots, wherein pre-processing comprises two or more of the mentioned steps.

9. The method of claim 1, wherein the preprocessing is performed and comprises filtering, application of a function, pre-treatment by applying an exponential fitting, bi-exponential fitting, multiple-exponential fitting, an inverse Laplace transform, a Gaussian decay fitting, compiling the data from the successive laser shots into a matrix, single vector, or other combined form, wherein pre-processing comprises two or more of the mentioned steps.

10. The method of claim 1, wherein the fluid parameter is obtained wherein manual or uni or multivariate analysis or cluster analysis or self-organising maps or neural nets or metaheuristic procedures are utilized to correlate the collected data, raw or pre-processed, to determine values for at least one fluid composition, salinity, different salt contents, viscosity, pour point, PVT properties, qualitative and quantitative sulfur content, qualitative and quantitative nitrogen content, qualitative and quantitative trace element content, qualitative and quantitative heavy metal content.

11. The method of claim 1, wherein said subjecting comprises controlling operation of the laser and a plurality of said spectrum detectors to simultaneously detect spectral emissions from the geological sample across a plurality of different spectral regions, and said analysing comprises determining the presence and amount of a plurality of different elements in the geological sample.

12. The method of claim 1, wherein the sample is a rock sample.

13. The method of claim 1, wherein each of the spectrum detectors comprises a spectrometer having a CCD detector associated therewith.

14. A system for analysing a geological sample comprising fluid contents and solid contents, comprising:
    i) a LIBS spectral data acquisition device for obtaining LIBS spectral information on at least the fluid contents of at least one location of the geological sample by subjecting at least the fluid contents of at least one location of the geological sample to a plurality of successive measurement shots of laser light, with each measurement shot at least partly vaporising and turning the portion of the fluid contents with said geological sample into plasma to cause emission and detecting said spectral emission after each said measurement shot with at least one spectrum detector to collect raw spectral data;

ii) one or more computer systems comprising at least one processor and a non-transitory computer-readable medium including a stored program comprising a set of instructions performed by the processor for carrying out steps to:

observing changes in the raw spectral data based on the plurality of successive measurement shots until a steady state of raw spectral data is reached, wherein the steady state indicates that the fluid contents are vaporized;

comparing an initial spectra that includes elemental contributions from the fluid contents to a final spectra taken after reaching the steady state; and determining at least one fluid parameter using the compared data; and iii) at least one device to display, print, and/or store as a non-transitory storage medium, results of the computations.

* * * * *